United States Patent [19]

Habiby

[11] 3,953,347

[45] Apr. 27, 1976

[54] NOVEL SULFUR-CONTAINING COMPOSITIONS

[75] Inventor: Emile Najib Habiby, Willowick, Ohio

[73] Assignee: The Lubrizol Corporation, Cleveland, Ohio

[22] Filed: Apr. 3, 1972

[21] Appl. No.: 240,795

Related U.S. Application Data

[63] Continuation-in-part of Ser. No. 178,803, Sept. 8, 1971, abandoned.

[52] U.S. Cl. ................................ 252/48.6; 260/125
[51] Int. Cl.² .................... C10M 1/38; C10M 3/32; C09B 49/00; C09B 59/00
[58] Field of Search ................... 260/125; 252/48.6

[56] References Cited
UNITED STATES PATENTS

| | | |
|---|---|---|
| 2,417,283 | 3/1947 | Zimmer et al. ................... 252/48.6 |
| 2,855,366 | 10/1958 | Manteuffel et al. ........... 252/48.6 X |
| 3,236,771 | 2/1966 | Matson .......................... 252/48.6 X |
| 3,455,896 | 7/1969 | Herder et al. .................. 252/48.6 X |

*Primary Examiner*—Delbert E. Gantz
*Assistant Examiner*—I. Vaughn
*Attorney, Agent, or Firm*—James W. Adams, Jr.; William H. Pittman

[57] ABSTRACT

Compositions suitable as replacements for sulfurized sperm oil as extreme pressure additives in lubricants are obtained by sulfurizing a mixture of at least one fatty acid ester (preferably an oil such as soybean oil), at least one $C_{8-36}$ aliphatic olefin (preferably an $\alpha$-olefin), and, optionally, at least one fatty acid (preferably unsaturated).

7 Claims, No Drawings

NOVEL SULFUR-CONTAINING COMPOSITIONS

This application is a continuation-in-part of copending application Ser. No. 178,803, filed Sept. 8, 1971 now abandoned.

This invention relates to new compositions of matter suitable for use as lubricant additives, and to methods for their preparation. More particularly, it relates to sulfurized compositions prepared by reacting, at about 100°–250°C., sulfur with a mixture comprising (A) 100 parts by weight of at least one fatty acid ester, (B) about 0–50 parts by weight of at least one fatty acid, and (C) about 25–400 parts by weight of at least one aliphatic olefin containing about 8–36 carbon atoms.

Sulfurized sperm oil has long been used as a lubricant additive, particularly to improve extreme pressure properties while providing excellent "slip" and some degree of rust inhibition in motor oils, gear lubricants, cutting and rolling oils. However, the United States Government has recently taken action to prevent the killing of whales, from which sperm oil is obtained, to avoid their becoming extinct. The only source of sperm oil has therefore "dried up" and it has become necessary to find substitutes for the sulfurized derivatives thereof, which can be cheaply and efficiently produced and which provide the same advantageous properties to lubricants.

A principal object of the present invention, therefore, is to provide a method for producing useful lubricant additives.

A further object is to produce sulfurized lubricant additives which improve extreme pressure properties.

Still another object is to produce compositions which may be substituted for sulfurized sperm oil as lubricant additives, and which provide the same properties as the sperm oil derivative.

Other objects will in part be obvious and will in part appear hereinafter.

As previously described, the method of this invention comprises the reaction of sulfur with a mixture of three reagents. Reagent A is at least one fatty acid ester. The term "fatty acid" as used herein refers to acids which may be obtained by hydrolysis of a naturally occurring vegetable or animal fat or oil. These are usually in the $C_{16-20}$ range and include palmitic acid, stearic acid, oleic acid, linoleic acid and the like.

Fatty acid esters which are useful as reagent A are primarily those with aliphatic alcohols, including monohydric alcohols such as methanol, ethanol, n-propanol, isopropanol, the butanols, etc., and polyhydric alcohols including ethylene glycol, propylene glycol, trimethylene glycol, neopentyl glycol, glycerol and the like. Particularly preferred are the fatty oils, that is, naturally occurring esters of glycerol with the above-noted long chain carboxylic acids, and synthetic esters of similar structure. Still more preferred are fatty oils derived from unsaturated acids, especially oleic and linoleic, including such naturally occurring animal and vegetable oils as lard oil, peanut oil, cottonseed oil, soybean oil, corn oil and the like.

Reagent B is at least one fatty acid as described above. It is usually an unsaturated fatty acid such as oleic or linoleic acid, and may be a mixture of acids such as is obtained from tall oil or by the hydrolysis of peanut oil, soybean oil or the like. The amount of reagent B is about 0–50 parts by weight per 100 parts of reagent A; that is, it is an optional ingredient. However, it improves the slip, rust inhibiting and extreme pressure properties of lubricants containing the sulfurized compositions of this invention, and so its presence (generally in the amount of about 2–8 parts by weight) is preferred.

Reagent C is at least one $C_{8-36}$ aliphatic olefin. About 25–400 parts, usually about 25–75 parts, of reagent C are present per 100 parts of reagent A. Terminal olefins, or $\alpha$-olefins, are preferred, especially those in $C_{12-20}$ range. Mixtures of these olefins are commercially available and such mixtures ae contemplated for use in this invention.

In addition to the above-described reagents, the reaction mixture may contain other materials. These may include, for example, sulfurization promoters, typically phosphorous-containing reagents such as phosphorous acid esters (e.g., triphenyl phosphite), and surface active agents such as lecithin.

The method of this invention comprises the reaction of a mixture of the above-noted reagents with sulfur at a temperature of about 100°–250°C., usually about 150°–210°C. The weight ratio of the combination of reagents A, B and C to sulfur is between about 5:1 and 15:1, generally between about 5:1 and 10:1.

The sulfurization reaction is effected by merely heating the reagents at the temperature indicated above, usually with efficient agitation and in an inert atmosphere (e.g., nitrogen). If any of the reagents, especially reagent C, are appreciably volatile at the reaction temperature, the reaction vessel may be sealed and maintained under pressure. It is frequently advantageous to add the sulfur portionwise to the mixture of the other reagents. While it is usually preferred that the reaction mixture consist entirely of the reagents previously described, the reaction may also be effected in the presence of an inert solvent (e.g., an alcohol, ether, ester, aliphatic hydrocarbon, halogenated aromatic hydrocarbon or the like) which is liquid within the temperature range employed. When the reaction temperature is relatively high, e.g., about 200°C., there may be some evolution of sulfur from the product which is avoided if a lower reaction temperature (e.g., about 150°–170°C.) is used. However, the reaction sometimes requires a longer time at lower temperatures and an adequate sulfur content is usually obtained when the temperature is at the high end of the recited range.

Following the reaction, insoluble by-products may be removed by filtration, usually at an elevated temperature (about 80°–120°C.). The filtrate is the desired sulfurized product.

In general, products prepared as described above and containing about 8–13% (by weight) sulfur are preferred for the purposes of this invention. It may sometimes be desirable, however, to employ products containing more sulfur, typically about 13–16% by weight. Also, it has been found that a product having improved solubility in bright stocks may be obtained by preparing a high-sulfur product of this type and diluting the same with a fatty oil such as lard oil to obtain a product having a lower sulfur content.

The method of this invention is illustrated by the following examples. All parts are by weight.

EXAMPLE 1

A mixture of 60 parts of commercial $C_{15-20}$ $\alpha$-olefins and 100 parts of lard oil is heated to 160°C., under nitrogen, and 12 parts of sulfur is added. The mixture is heated at 65°–200°C. and an additional 6.5 parts of sulfur is added. Heating is continued for 4 hours, after which the mixture is cooled to 100°C. and filtered to yield the desired product which contains 9.0% sulfur.

EXAMPLE 2

To a mixture of 100 parts of soybean oil and 50 parts of 1-hexadecene at 165°C., under nitrogen, is added over 20 minutes, with stirring, 20.6 parts of sulfur. An exothermic reaction occurs which causes the temperature to rise to 200°C. It is heated at 175°–200°C. for 6 hours, cooled to 110°C. and filtered to yield the desired product which contains 11.1% sulfur.

EXAMPLE 3

A mixture of 100 parts of soybean oil and 50 parts of commercial $C_{16}$ α-olefins is heated to 175°C. under nitrogen and 17.4 parts of sulfur is added gradually, whereupon an exothermic reaction causes the temperature to rise to 205°C. The mixture is heated at 188°–200°C. for 5 hours, allowed to cool gradually to 90°C. and filtered to yield the desired product containing 10.13% sulfur.

EXAMPLE 4

Following the procedure of Example 3, a sulfurized product is prepared from 100 parts of soybean oil, 50 parts of commercial $C_{15-18}$ α-olefins and 17.4 parts of sulfur. It contains 10.1% sulfur.

EXAMPLE 5

Following the procedure of Example 3, a product containing 10.13% sulfur is obtained by the reaction of 100 parts of soybean oil, 50 parts of commercial $C_{15-20}$ α-olefins and 17.9 parts of sulfur.

EXAMPLE 6

Following the procedure of Example 3, a product containing 9.69% sulfur is obtained from 100 parts of soybean oil, 100 parts of commercial $C_{22-28}$ α-olefins and 23.2 parts of sulfur.

EXAMPLE 7

Following the procedure of Example 3, a product containing 10.16% sulfur is obtained from 100 parts of cottonseed oil, 33.3 parts of commercial $C_{15-20}$ α-olefins and 15.6 parts of sulfur.

EXAMPLE 8

Following the procedure of Example 3, a product containing 8.81% sulfur is obtained from 100 parts of a triglyceride having an iodine number of 85–95, 25 parts of commercial $C_{15-18}$ α-olefins and 14.5 parts of sulfur.

EXAMPLE 9

A mixture of 100 parts of soybean oil, 50 parts of commercial $C_{15-18}$ α-olefins, 1.17 part of triphenyl phosphite and 17.4 parts of sulfur is heated for 16 hours at 145°–165°C., under nitrogen. It is then cooled to room temperature, reheated to 100°C. and filtered with the addition of a filter aid material. The filtered product contains 10.13% sulfur.

EXAMPLE 10

A mixture of 100 parts of soybean oil, 3.7 parts of tall oil acid and 46.3 parts of commercial $C_{15-18}$ α-olefins is heated to 165°C. under nitrogen, and 17.4 parts of sulfur is added. The temperature of the mixture rises to 191°C. It is maintained at 165°–200°C. for 7 hours and is then cooled to 90°C. and filtered. The product contains 10.13% sulfur.

EXAMPLE 11

Following the procedure of Example 10, a product containing 10.39% sulfur is obtained from 100 parts of soybean oil, 4 parts of tall oil acid, 46.3 parts of commercial $C_{15-18}$ α-olefins and 20.6 parts of sulfur.

EXAMPLE 12

Following the procedure of Example 10, a product containing 10.6% sulfur is obtained from 100 parts of soybean oil, 5.25 parts of tall oil acid, 44.8 parts of commercial $C_{15-18}$ α-olefins and 17.4 parts of sulfur.

EXAMPLE 13

Following the procedure of Example 10, a product containing 10.4% sulfur is obtained from 100 parts of peanut oil, 5.26 parts of tall oil acid, 45 parts of commercial $C_{15-18}$ α-olefins and 17.5 parts of sulfur.

EXAMPLE 14

Following the procedure of Example 10, a product containing 12.41% sulfur is obtained from 100 parts of soybean oil, 5.35 parts of tall oil acid, 46.3 parts of commercial $C_{15-18}$ α-olefins and 26.8 parts of sulfur.

EXAMPLE 15

Following the procedure of Example 10, a product containing 9.98% sulfur is obtained from 100 parts of soybean oil, 4.11 parts of tall oil acid, 44.8 parts of a mixture of $C_{12-16}$ fractions from the polymerization of isobutene, and 20.8 parts of sulfur.

EXAMPLE 16

A product containing 13.7% sulfur is obtained from 100 parts of soybean oil, 5.4 parts of tall oil acid, 46.2 parts of commercial $C_{15-18}$ α-olefins, 1.5 parts of triphenyl phosphite and 25 parts of sulfur following the procedure of Example 10 except that a temperature range of 135°–165°C. is employed.

EXAMPLE 17

Following the procedure of Example 10, a product containing 9.54% sulfur is obtained from 100 parts of soybean oil, 5.53 parts of tall oil acid, 50.2 parts of commercial $C_{15-18}$ α-olefins, 3.18 parts of lecithin and 18.4 parts of sulfur.

EXAMPLE 18

A product is prepared from 100 parts of soybean oil, 5.4 parts of tall oil acid, 46.3 parts of commercial $C_{15-18}$ α-olefin and 24.8 parts of sulfur, following the procedure of Example 10 except that the temperature is 155°–203°C. and the product is filtered at 110°C. It contains 14.45% sulfur.

EXAMPLE 19

A product containing 13.5% sulfur is prepared according to the method of Example 18. To 252 parts of this product is added 88.3 parts of lard oil. The resulting composition, which has improved solubility in bright stocks, contains 10% sulfur.

The compositions of this invention can be employed in a variety of lubricating compositions based on diverse oils of lubricating viscosity, including natural and synthetic lubricating oils and mixtures thereof. The lubricating compositions contemplated include principally crank-case lubricating oils for spark-ignited and compression-ignited internal combustion engines including automobile and truck engines, two-cycle engine lubricants, aviation piston engines, marine and railroad diesel engines, and the like. However, automatic transmission fluids, transaxle lubricants, gear lubricants, metal-working lubricants, hydraulic fluids, and other lubricating oil and grease compositions can benefit from the incorporation of the present compositions.

Natural oils include animal oils and vegetable oils (e.g., castor oil, lard oil) as well as solvent-refined or acid-refined mineral lubricating oils of the paraffinic, naphthenic, or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, etc.); alkylbenzenes (e.g., dodecylbenzenes, tetradecylbenzenes, dinonylbenzenes, di-(2-ethylhexyl) benzenes, etc.); polyphenyls (e.g., biphenyls, terphenyls, etc.); and the like. Alkylene oxide polymers and interpolymers and derivatives thereof where the terminal hydroxyl groups have been modified by esterification, etherification, etc., constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$Oxo acid diester of tetraethylene glycol. Another suitable class of synthetic lubricating oils comprises the esters of dicarboxylic acids (e.g., phthalic acid, succinic acid, maleic acid, azelaic acid, suberic acid, sebacic acid, fumaric acid, adipic acid, linoleic acid dimer, etc.) with a variety of alcohols (e.g., butyl alcohol, hexyl alcohol, dodecyl alcohol, 2-ethylhexyl alcohol, pentaerylthritol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like. Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-tetraethyl) silicate, tetra-(p-tert-butylphenyl) silicate, hexyl-(4-methyl-2-pentoxy)-disiloxane, poly(-methyl)-siloxanes, poly(methylphenyl)-siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans, and the like.

In general, about 0.05–20.0 parts (by weight) of the composition of this invention is dissolved in 100 parts of oil to produce a satisfactory lubricant. The invention also contemplates the use of other additives in combination with the products of this invention. Such additives include, for example, detergents and dispersants of the ash-containing or ashless type, oxidation inhibiting agents, pour point depressing agents, auxiliary extreme pressure agents, color stabilizers and anti-foam agents.

The ash-containing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50°C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent, a phenolic promoter compound, and a small amount of water and carbonating the mixture at an elevated temperature such as 60°–200°C.

Ashless detergents and dispersants are illustrated by the interpolymers of an oil-solubilizing monomer, e.g., decyl methacrylate, vinyl decyl ether, or high molecular weight olefin, with a monomer containing polar substituents, e.g., aminoalkyl acrylate or poly-(oxyethylene)-substituted acrylate; the amine salts, amides, and imides of oil-soluble monocarboxylic or dicarboxylic acids such as stearic acid, oleic acid, tall oil acid, and high molecular weight alkyl or alkenyl-substituted succinic acid. Especially useful as ashless detergents are the acylated polyamines and similar nitrogen compounds containing at least about 54 carbon atoms as described in U.S. Pat. No. 3,272,746; reaction products of such compounds with other reagents including boron compounds, phosphorus compounds, epoxides, aldehydes, organic acids and the like; and esters of hydrocarbonsubstituted succinic acids as described in U.S. Pat. No. 3,381,022.

Auxiliary extreme pressure agents and corrosion-inhibiting and oxidation-inhibiting agents are exemplified by chlorinated aliphatic hydrocarbons such as chlorinated wax; organic sulfides and polysulfides such as benzyl disulfide, bis(chlorobenzyl) disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl) phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

It is possible to form the lubricants of this invention by dissolving the various additives, or oil solutions thereof, directly in a mineral oil. However, it is generally more convenient and is preferred to prepare additive concentrates containing two or more of the desired additives, and to dissolve these concentrates in the mineral oil to form the final lubricating composition.

Typical lubricating compositions according to this invention are listed in Tables I–III. All amounts listed, except those for mineral oil, are exclusive of oil present as diluent.

TABLE I

| | Parts by weight | | | | | |
|---|---|---|---|---|---|---|
| | A | B | C | D | E | F |
| Mineral oil (100 neutral base) | 95 | 95 | 95 | 95 | 95 | 95 |
| Product of Example 1 | 5 | — | — | — | — | — |
| Product of Example 4 | — | 5 | — | — | — | — |
| Product of Example 5 | — | — | 5 | — | — | — |
| Product of Example 9 | — | — | — | 5 | — | — |
| Product of Example 10 | — | — | — | — | 5 | — |
| Product of Example 11 | — | — | — | — | — | 5 |

TABLE II

| | Parts by weight | | | |
|---|---|---|---|---|
| | G | H | J | K |
| Mineral oil (SAE 80) | — | — | 94.38 | — |
| Mineral oil (SAE 90) | 95.12 | 95.13 | — | 95.24 |
| Product of Example 1 | 3.78 | — | — | — |
| Product of Example 12 | — | 3.60 | 5.25 | 3.28 |
| Product formed by reacting hydroxypropyl 0,0-di-(4-methyl-2-pentyl)phosphorodithioate with phosphorus pentoxide and subsequently neutralizing with $C_{11-14}$ tertiary alkyl primary amine mixture | — | — | — | 0.43 |
| 4-Methyl-2-pentyl phosphite | 0.27 | 0.30 | — | 0.26 |
| Sulfurized isobutene | 0.59 | 0.70 | — | 0.56 |
| Oleyloxazine | 0.24 | 0.27 | — | 0.23 |
| Styrene-maleic anhydride copolymer, partially esterified with $C_{4-18}$ alcohols and neutralized with $C_{11-14}$ tertiary alkyl primary amine mixture | — | — | 0.37 | — |
| Silicone anti-foam agent | 0.02 | 0.02 | 0.04 | 0.02 |

TABLE III

| | Parts by weight | | |
|---|---|---|---|
| | L | M | N |
| Mineral oil (industrial oil base) | 93.45 | — | — |
| Mineral oil (tractor oil base) | — | 96.44 | 95.94 |
| Product of Example 13 | 5.0 | 1.5 | 1.5 |
| Zinc salt of 0,0-di($C_{12-14}$ alkyl)-phosphorodithioic acid | 0.5 | 1.0 | 1.5 |
| $C_{11-14}$ tertiary alkyl primary amine salt of $C_{14-18}$ alkyl phosphoric acid | 0.3 | 0.3 | 0.3 |
| Sulfurized isobutene | 0.25 | 0.26 | 0.26 |
| Poly-(alkyl methacrylate) pour point depressant | 0.5 | 0.5 | 0.5 |
| Silicone anti-foam agent | 0.005 | 0.005 | 0.005 |

In the lubricating compositions listed above, the sulfurized compositions of this invention provide the properties previously imparted by sulfurized sperm oil.

What is claimed is:

1. A sulfurized composition of matter prepared by reacting, at about 100°–250°C., sulfur with a mixture comprising (A) 100 parts by weight of at least one fatty acid ester of a polyhydric alcohol, (B) about 2–50 parts by weight of at least one fatty acid, and (C) about 25–400 parts by weight of at least one aliphatic α-olefin containing about 8–36 carbon atoms.

2. A composition according to claim 1 wherein reagent A is at least one fatty oil.

3. A composition according to claim 2 wherein reagent C is at least one $C_{12-20}$ α-olefin.

4. A composition according to claim 3 wherein reagent B is tall oil acid and is present in the amount of about 2–8 parts by weight.

5. A composition according to claim 3 wherein reagent A is soybean oil.

6. A composition according to claim 5 wherein reagent B is tall oil acid and is present in the amount of about 2–8 parts by weight.

7. A composition according to claim 6 wherein reagent C is present in the amount of about 25–75 parts by weight.

* * * * *

Notice of Adverse Decision in Interference

In Interference No. 100,000, involving Patent No. 3,953,347, E. N. Habiby, NOVEL SULFUR-CONTAINING COMPOSITIONS, final judgment adverse to the patentee was rendered Jan. 6, 1984, as to claims 1 and 3.
[*Official Gazette March 13, 1984.*]